United States Patent
Yamashita et al.

(10) Patent No.: US 9,354,244 B2
(45) Date of Patent: May 31, 2016

(54) METHOD FOR EVALUATING HUMAN BLASTOCYST BY NOREPINEPHRINE LEVEL IN BLASTOCYST CULTURE SOLUTION

(71) Applicant: Naoki Yamashita, Kanagawa (JP)

(72) Inventors: Naoki Yamashita, Kanagawa (JP); Kumiko Nakata, Kanagawa (JP)

(73) Assignee: Naoki Yamashita, Kanagawa (JP)

( * ) Notice: Subject to any disclaimer, the term of this patent is extended or adjusted under 35 U.S.C. 154(b) by 230 days.

(21) Appl. No.: 14/041,338

(22) Filed: Sep. 30, 2013

(65) Prior Publication Data

US 2014/0249363 A1    Sep. 4, 2014

(30) Foreign Application Priority Data

Mar. 1, 2013  (JP) ................. 2013-040989

(51) Int. Cl.
  *A61B 17/435*  (2006.01)
  *G01N 33/94*  (2006.01)
(52) U.S. Cl.
  CPC ........... *G01N 33/9433* (2013.01); *A61B 17/435* (2013.01); *G01N 2800/367* (2013.01); *G01N 2800/52* (2013.01)
(58) Field of Classification Search
  CPC ................... G01N 33/9433; G01N 2800/367; G01N 2800/52; A61B 17/435
  See application file for complete search history.

(56) References Cited

FOREIGN PATENT DOCUMENTS

JP       2005-229923       9/2005

OTHER PUBLICATIONS

Katz-Jaffe et al., "Analysis of Protein Expression (Secretome) by Human and Mouse Preimplantation Embryos," Fertility and Sterility, vol. 86, No. 3, pp. 678-685, Sep. 2006.
Xiao-Yan et al., "A Highly Sensitive Eleotrochemiluminescence Immunoassay for Detecting Human Embryonic Human Chorionic Gonadotropin in Spent Embryo Culture Media During IVF-ET Cycle," J. Assist. Reprod. Genet., 6 pages, Dec. 2012.
(Continued)

*Primary Examiner* — Navin Natnithithadha
*Assistant Examiner* — Kaylee Wilson
(74) *Attorney, Agent, or Firm* — Margaret B. Brivanlou; Leslie A. Serunian; King & Spalding LLP

(57) ABSTRACT

The invention provides a new method for evaluating transfer embryos including blastocysts used for in vitro fertilization in fertility treatment, and a method for evaluating transfer embryos using a new biomarker necessary for evaluation. The method comprises the steps of (a) providing a test object, for example, a culture solution of a human blastocyst, containing norepinephrine (noradrenaline) released from a transfer embryo, such as a human blastocyst, obtained from a subject; (b) quantitatively analyzing norepinephrine in the test object by a combination of ultra high performance liquid chromatography and mass spectrometry or the like; (c) predicting the quality of the transfer embryo based on the amount of norepinephrine from analysis results obtained; and (d) transferring the embryo into a suitable female recipient for implantation, if the transfer embryo is predicted to be of good quality and/or to lead to the establishment of a viable pregnancy based on step (c).

15 Claims, 13 Drawing Sheets
(4 of 13 Drawing Sheet(s) Filed in Color)

(56) References Cited

OTHER PUBLICATIONS

Naoki Yamashita (Submitter name), English translation of Submission of Certificate of Exception of Loss of Novelty for Japanese Patent Application No. JP2013-40989 to Japanese Patent Office, along with the original Submission of Certificate of Exception as filed in the Japanese language, with associated publications related to the Certificate submission, Mar. 19, 2013, 46 pages.

English translation of Program of the 57th Scientific Meeting and Annual Meeting of Japan Society for Reproductive Medicine Conference Program, Edited and Published by Japan Society for Reproductive Medicine, vol. 57, No. 4, No. O-031, K. Nakata et al., "—New finding in embryo culture—Norepinephrine is detected from blastocyst culture solution", Publication date: Oct. 2, 2012 (Print date: Sep. 25, 2012); Conference date: Nov. 8-9, 2012, 5 pages.

K. Nakata et al., English translation of the Slide Presentation titled "New finding in Embryo Culture—Norepinephrine is Detected from Blastocyst Culture Solution", presented at the 57th Scientific Meeting and Annual Meeting of Japan Society for Reproductive Medicine Conference, Nov. 8-9, 2012, 16 pages.

Figure 1

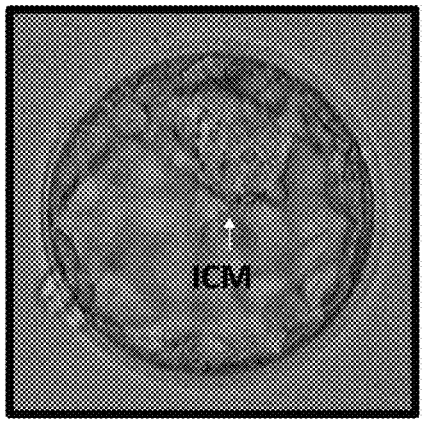

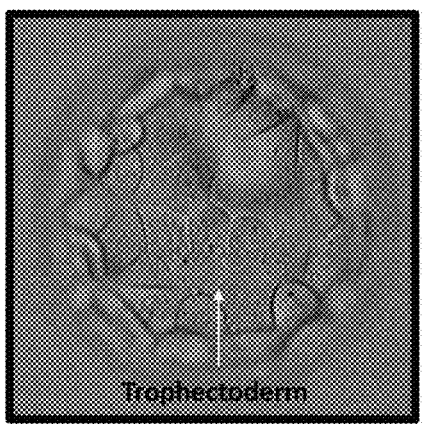

Grading of blastocysts
(Application of Gardner classification)

Morphological evaluation of inner cell mass (ICM)
A: Tightly packed, many cells
B: Loosely grouped, several cells
C: Very few cells Morphological evaluation of trophectoderm (TE)
A: Many cells forming a cohesive TE.
B: Few cells forming a loose TE.
C: Very few cells Grading (comprehensive evaluation based on ICM and TE)

Grade 1 : AA
Grade 2 : AB, BA, BB
Grade 3 : Other than the above

Gardner evaluation of blastocysts

Blastocysts A and B are:

- derived from ova collected at the same cycle in the same patient
- frozen at the same growth rate and at the same point in time (at 123 hours after in vitro fertilization) in an in vitro culture solution
- the same in diameter (160 μm)

Which of the blastocysts is selected for transfer?

Search for biomarker in blastocyst culture solution using ultra high performance liquid chromatography and mass spectrometry Result 1: Comparison of components between sample and culture solution

Figure 8

Result 4: Correlation between pregnancy and norepinephrine

| Sample size | Average age | Average number of transfer embryos | Blood hormone value before transfer | | Endometrium thickness in transfer (mm) | Blood human chorionic gonadotropin on date of implantation determination βhCG (mIU/ml) | Norepinephrine value Norepinephrine Area NA ±SD CPU |
|---|---|---|---|---|---|---|---|
| | | | Estrogen E2(mg/ml) | Progesterone P4(ng/ml) | | | |
| Pregnancy continuation-delivery | 11 | 33 | 1 | 179.8 | 19.0 | 9.7 | 77.1 | 1458.8±880.8 a |
| Only pregnancy reaction (No implantation) | 8 | 38.375 | 1.3 | 195.9 | 15.8 | 9.8 | 9.1 | 8612.8±7021.4 b |
| Growth stopped during culture | 7 | — | — | — | — | — | — | 8502.0±4681.4 b | a-b: P<0.05

Figure 9
Result 5: Photographs of immunofluorescently stained mouse blastocysts
A Expanded blastocysts
merge | Dopamine β-hydroxylase | PI/nuclear staining
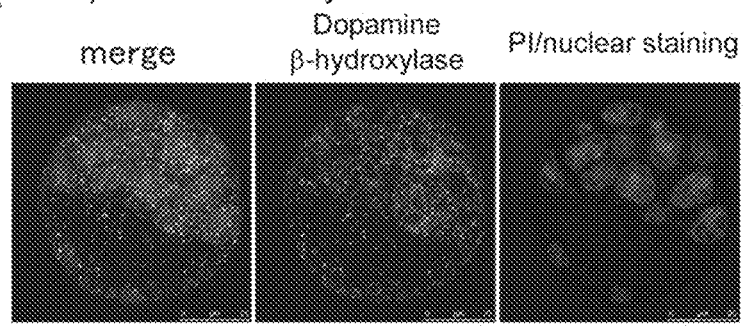
B Hatching blastocysts
merge | Dopamine β-hydroxylase | PI/nuclear staining
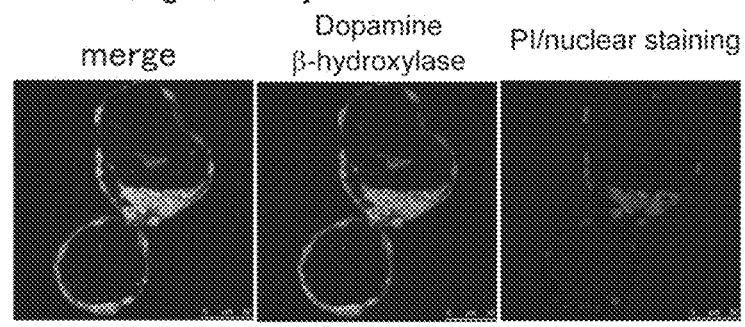

Result 7: Photographs of immunofluorescently stained rat blastocysts

Expanded blastocysts merge | Dopamine β-hydroxylase | PI/Nuclear staining

Result 8: Photographs of immunofluorescently stained human good blastocysts and degenerated blastocysts merge | Dopamine β-hydroxylase | PI/Nuclear staining

Figure 13

Result 9: In vitro development rates of in vitro fertilized mouse embryos cultured in vitro under conditions of various concentrations of norepinephrine

| Norepinephrine (mM) | number of pronucleus stage embryos [pronucleus(PN) stage] | Number of cleavage embryos [cleavage embryos] (%) | Number of 4-cel stage embryos [4 cell stage] (%) | Number of morulae [morula] (%) | Number of blastocysts [blastocyst] (%) |
|---|---|---|---|---|---|
| 0.0 | 61 | 55(90.0) a | 53(86.9) c | 53(86.9) e | 53(86.9) g |
| 0.01 | 57 | 53(93.0) a | 51(89.5) c | 49(86.0) e | 41(71.9) g |
| 0.05 | 34 | 26(76.5) a | 7(20.6) d | 0(0) f | 0(0) h |
| 0.1 | 50 | 0(0) b | 0(0) d | 0(0) f | 0(0) h |
| 1.0 | 22 | 0(0) b | 0(0) d | 0(0) f | 0(0) h | a-b, c-d, e-f, g-h: $P<0.01$

Result 10: Microscope images of in vitro fertilized mouse embryo cultured in vitro under conditions of various concentrations of norepinephrine Mouse blastocyst

METHOD FOR EVALUATING HUMAN BLASTOCYST BY NOREPINEPHRINE LEVEL IN BLASTOCYST CULTURE SOLUTION

TECHNICAL FIELD

The present invention relates to a method for evaluating transfer embryos for in vitro fertilization, and more specifically to a method for sorting an embryo with a high implantation rate by the quantitative determination of norepinephrine secreted by the embryos or from the results of the quantitative determination.

BACKGROUND ART

The phenomenon of "tendency to marry later" is generally recognized to not only reduce the reproductive period but also have the possibility of increasing disabilities associated with pregnancy/delivery, while 52.6% of all births in Japan have been taken by women in their thirties/forties ("Population Survey Report 2004" conducted by the Ministry of Health, Labour and Welfare). The upshot is that the higher childbearing age accompanied by tendency to marry later is behind a tendency of infertility, and the estimated total number of patients under fertility treatment reported by the Ministry of Health, Labor and Welfare exceeded 460 thousand as of FY 2002 and is predicted to continue to increase also in the future. Assisted reproduction technologies, such as artificial insemination, in vitro fertilization, and microinsemination, as important breakthroughs for infertility increase year by year in the number of performed cases even though they are not covered by public health insurance, and the Research Committee of Japan Society of Obstetrics and Gynecology reports that the total number of patients undergoing in vitro fertilization and microinsemination in 2004 was 78,000 or more and this number is two times or more the total number of the same patients in 1997. The flow of tendency to marry later appears as not readily changing; thus, it is expected to hold the important key to reverse the birthrate decline to address the need of men and women desiring pregnancy at advanced ages, further increasing the degree of dependency on assisted reproduction technologies.

According to data of the Ministry of Health, Labour and Welfare summarized in 2003, men and women each have an infertility cause ratio of 50%. Defects in spermatogenesis account for 90% or more of the cause of male infertility, and the remaining 10% is ascribed to sexual dysfunction. The defects in spermatogenesis refer to a sperm count lower than the reference, a low sperm density, a poor sperm motility, a high malformation rate of sperm, and the like, and as their causes are known aging, influences of environmental hormones, lifestyle-related diseases, zinc deficiency due to an unbalanced dietary life, stress, smoking, and the like although about 60 percent of male infertility is unexplained. On the other hand, the causes of female infertility are roughly classified into 3 types: an ovulation disorder in which ovulation from the ovary does not occur, a tubal disorder in which fertilization is interrupted by the blocked oviduct after ovulation or the like, and a disorder of implantation in which implantation in the uterus cannot occur after fertilization.

A relatively simple technique adopted by mainly targeting infertility ascribed to the male side is artificial insemination and specifically involves sorting collected sperms followed by injection into the uterine cavity using a device, and thereby aiming at in vivo fertilization. A method performed in cases where it is probably difficult to carry out in vivo fertilization, such as oviduct occlusion and oligospermia/asthenospermia, is called in vitro fertilization; especially, in vitro fertilization—embryo transfer is now a most widely used method.

The administration of in vitro fertilization is roughly divided into 3 steps. First, in order to efficiently induce ovulation, various hormonal agents, ovulation inducing agents, or the like are each administered to a female patient to elicit ovulation. Next, mature ova are sucked/removed by inserting a needle into an ovarian follicle while being confirmed with a transvaginal ultrasonographic image, and fertilized by mixing the collected ova with separately collected and purified sperms in a culture solution. When the fertilization ability of the sperms is considerably weak, microfertilization is performed in which the sperms are each penetrated into an egg artificially under a microscope. In the final step, a fertilized ovum (embryo) after sorting is transferred into the uterus, thereby aiming at implantation-pregnancy.

A fertilized ovum grown to a stage of about 5 to 6 days after the start of cleavage is called a blastocyst, and an embryo grown to the blastocyst implants in the endometrium in the case of spontaneous pregnancy. Blastocyst transfer involving transferring an embryo to the uterus at a culture stage close to the timing of implantation in spontaneous pregnancy is generally considered to show an enhanced pregnancy rate compared to transfer using a cleavage-stage embryo at 2 to 3 days after fertilization.

The number of embryos transferred at a time is controversial: there is a case where a plurality of blastocysts are transferred to increase the rate of success in pregnancy, which would simultaneously elevate the possibility of multiple pregnancy, that is, take a big risk of increasing the rate of occurrence of pregnancy hypertension syndromes and complications in the mother's body as well as increasing the percentage of occurrence of abortion, premature birth, or disability. According to the view of Japan Society of Obstetrics and Gynecology announced in 2008, the transferred embryo is single in principle, and double embryo transfer is accepted for women aged 35 years or more, women whose pregnancy has failed twice or more in a row, or the like.

In the step of ovum collection, a plurality of mature unfertilized ova can be potentially collected, in which case a better blastocyst suitable for implantation needs to be selected from a plurality of embryos at a stage in which they have been grown into a state enabling transfer after fertilization, and evaluation by morphological observation is the only way presently used (FIGS. 1 and 2).

As clinical case examples showing the difficulty of selection of a blastocyst, in a case in which are obtained two good blastocysts derived from ova collected at the same cycle in the same patient and frozen at the same growth rate and at the same point in time (at 123 hours after in vitro fertilization) in an in vitro culture solution, many examples have been experienced such as in which pregnancy did not occur for the blastocyst selected for first transfer and pregnancy occurred as a result of performing second transfer using the other blastocyst, in sites of fertility treatment (FIG. 3). Despite that the two blastocysts had entirely the same evaluation results, pregnancy did not occur in the first transfer and implantation occurred in the latter transfer, showing the limitation of the current evaluation method; this is why a highly precise evaluation method correlated with improvement in the pregnancy rate has been looked forward to.

Most desirable in evaluating a blastocyst is it that noninvasive determination is possible without using an embryo itself as a test object, and a secreted material from an embryo contained in the culture solution is an important analyte meeting such requirements. Ubiquitin is identified in a report examining protein biomarkers contained in culture solutions of human and mouse embryos using a time-of-flight mass spectrometer (Non-patent Document 1); however, no relation with the pregnancy rate is described. A similar report suggests a correlation between the concentration of β-human chorionic gonadotropin (βhCG) (which is known to be produced in the syncytiotrophoblastic layer (a part of the placenta) of a fetus from immediately after conception) in an embryo culture solution and the pregnancy rate from the results of examining βhCG by an electrochemiluminescent immunoassay (ECLIA) (Non-patent Document 2); however, there is no finding that a fertilized ovum and an embryo secrete norepinephrine during development.

As an example of simply and effectively performing the sorting of a good ovum for in vitro fertilization, is publicly available a method for detecting a refractile body as an abnormal morphology in a pre-fertilized ovum (Patent Document 1), but its invasive properties into an ovum are undeniable in that it is essential for detection to expose an ovum to excitation light from a fluorescent microscope, a confocal laser microscope, or the like.

Given the economic/psychological burden on a patient, since in vitro fertilization is said to cost 250,000 to 800,000 yen or more for each fertilization, it is of extremely high significance and a deep challenge to more reliably select a blastocyst most suitable for implantation to aim for pregnancy by fewer times of transfer. Popularization of a new technology for exactly evaluating a blastocyst will relieve clinicians from the dilemma between multiple conception due to the transfer of a plurality of embryos and the enhanced pregnancy rate, and also can serve as the impetus for a patient thinking twice about fertility treatment for economic reasons to step out into the start of the treatment because it can be expected to reduce the number of in vitro fertilizations, that is, cost, required until establishment of pregnancy.

PRIOR ART DOCUMENTS

Patent Documents

Patent Document 1
Japanese unexamined Patent Application Publication No. 2005-229923

Non-patent Documents

Non-Patent Document 1
Katz-Jaffe M G, et al., (2006) Fertil Steril. September; 86(3): 678-85.
Non-Patent Document 2
Xiao-Yan C, et al., (2012) J Assist Reprod Genet. December 29. [Epub ahead of print]

SUMMARY OF THE INVENTION

The present invention provides a new method for evaluating transfer embryos including blastocysts used for in vitro fertilization in fertility treatment, and a method for evaluating transfer embryos using a new biomarker necessary for evaluation.

The present inventors have conducted intensive studies for solving the above problems. In these processes, the culture solution discarded after the culture of blastocysts was used as a test object to identify components specifically contained in the culture solution by analysis using ultra high performance liquid chromatography and further perform the quantitative determination thereof; as a result, it has been found after a great deal of trial and error that norepinephrine (noradrenaline) is a component deserving attention. As a result of further intensive investigations, it has been found that a significant difference exists between the amount of norepinephrine secreted into the culture solution by a group of blastocysts implanting after transfer and resulting in the continuation of pregnancy and the secretion amount of norepinephrine by blastocysts not implanting after transfer.

In addition, as a result of studying human well-grown blastocysts and degenerated blastocysts (blastocysts not normally grown) fluorescent-immunohistochemically, dopamine β-hydroxylase as an enzyme converting dopamine to norepinephrine has been confirmed to be intracellularly expressed in both inner cell mass and trophoblastic cells for the good blastocysts. For the degenerated blastocysts, strong expression has been confirmed in blastomeres whose division is stopped, and extracellular expression has also been confirmed.

The above observation is the first finding showing that norepinephrine as a neurotransmitter secreted from the brain stem and the adrenal cortex in an adult is produced in an embryo at an early stage of development. In other words, the present inventors have discovered a new biomarker for evaluating human blastocysts by the above technique, and have succeeded in the establishment of a new method for evaluating human blastocysts, enabling the selection of an embryo preferentially transferred when a plurality of morphologically well-grown embryos are obtained.

Specifically, the present invention relates to:

[1] a method for evaluating a transfer embryo for in vitro fertilization, comprising steps of:

(1) providing a test object containing norepinephrine released from the transfer embryo, obtained from a subject;

(2) quantitatively analyzing norepinephrine in the test object; and (3) predicting the quality of the transfer embryo based on the amount of norepinephrine from analysis results obtained.

The above method can further comprise the step of transferring or inserting the embryo into a suitable female recipient (patient) for implantation, if the transfer embryo is predicted to be of good quality and/or to lead to the establishment of a viable pregnancy, for example, based on the determination or quantification of norepinephrine in the test object as described herein. Thereafter, the embryo will implant and develop in the uterus in accordance with a successful pregnancy.

The present invention also relates to:

[2] the method according to [1] above, wherein the test object is a culture solution of the transfer embryo;

[3] the method according to [1] above, wherein the transfer embryo is a human blastocyst;

[4] the method according to [1] above, wherein the step of quantitative analysis is a combination of ultra high performance liquid chromatography and mass spectrometry and comprises a step of quantifying the amount of norepinephrine by peak area values by multivariate analysis of the analysis results;

[5] the method according to [1] above, wherein a norepinephrine level (peak area) below 5,100 CPU (count per unit) indicates a state in which the growth of a human blastocyst is good, and a norepinephrine level below 2,400 CPU (count per unit) indicates a high probability of pregnancy after blastocyst transfer;

[6] the method according to [1] above, wherein a norepinephrine level (peak area) exceeding 8,500 CPU (count per unit) indicates a state in which the growth of a human blastocyst is stopped, or a low probability of pregnancy after blastocyst transfer.

[7] the method according to [2], wherein the transfer embryo is a human blastocyst;

[8] the method according to [2], wherein the step of quantitative analysis is a combination of ultra high performance liquid chromatography and mass spectrometry and comprises a step of quantifying the amount of norepinephrine by peak area values by multivariate analysis of the analysis results;

[9] the method according to [3], wherein the step of quantitative analysis is a combination of ultra high performance liquid chromatography and mass spectrometry and comprises a step of quantifying the amount of norepinephrine by peak area values by multivariate analysis of the analysis results;

[10] the method according to [7], wherein the step of quantitative analysis is a combination of ultra high performance liquid chromatography and mass spectrometry and comprises a step of quantifying the amount of norepinephrine by peak area values by multivariate analysis of the analysis results;

[11] the method according to [2], wherein a norepinephrine level (peak area) below 5,100 CPU (count per unit) indicates a state in which the growth of a human blastocyst is good, and a norepinephrine level below 2,400 CPU (count per unit) indicates a high probability of pregnancy after blastocyst transfer;

[12] the method according to [3], wherein a norepinephrine level (peak area) below 5,100 CPU (count per unit) indicates a state in which the growth of a human blastocyst is good, and a norepinephrine level below 2,400 CPU (count per unit) indicates a high probability of pregnancy after blastocyst transfer;

[13] the method according to [4], wherein a norepinephrine level (peak area) below 5,100 CPU (count per unit) indicates a state in which the growth of a human blastocyst is good, and a norepinephrine level below 2,400 CPU (count per unit) indicates a high probability of pregnancy after blastocyst transfer;

[14] the method according to [7], wherein a norepinephrine level (peak area) below 5,100 CPU (count per unit) indicates a state in which the growth of a human blastocyst is good, and a norepinephrine level below 2,400 CPU (count per unit) indicates a high probability of pregnancy after blastocyst transfer;

[15] the method according to [8], wherein a norepinephrine level (peak area) below 5,100 CPU (count per unit) indicates a state in which the growth of a human blastocyst is good, and a norepinephrine level below 2,400 CPU (count per unit) indicates a high probability of pregnancy after blastocyst transfer;

[16] the method according to [2], wherein a norepinephrine level (peak area) exceeding 8,500 CPU (count per unit) indicates a state in which the growth of a human blastocyst is stopped, or a low probability of pregnancy after blastocyst transfer;

[17] the method according to [3], wherein a norepinephrine level (peak area) exceeding 8,500 CPU (count per unit) indicates a state in which the growth of a human blastocyst is stopped, or a low probability of pregnancy after blastocyst transfer;

[18] the method according to [4], wherein a norepinephrine level (peak area) exceeding 8,500 CPU (count per unit) indicates a state in which the growth of a human blastocyst is stopped, or a low probability of pregnancy after blastocyst transfer;

[19] the method according to [5], wherein a norepinephrine level (peak area) exceeding 8,500 CPU (count per unit) indicates a state in which the growth of a human blastocyst is stopped, or a low probability of pregnancy after blastocyst transfer; and the method according to [7], wherein a norepinephrine level (peak area) exceeding 8,500 CPU (count per unit) indicates a state in which the growth of a human blastocyst is stopped, or a low probability of pregnancy after blastocyst transfer.

Effect of the Invention

According to the present invention, a method is provided for more accurately and noninvasively evaluating well-grown embryos for in vitro fertilization. In other words, it not only enables the reduction of the number of in vitro fertilizations until establishment of pregnancy by the selection of an embryo having high potential to implant, but also provides valuable information for making a decision for clinicians in restricting the transfer of a plurality of embryos in which multiple conception would be risked in order to increase the pregnancy rate.

BRIEF DESCRIPTION OF DRAWINGS

The patent or patent application file contains at least one drawing executed in color. Copies of this patent or patent application publication with color drawing(s) will be provided by the U.S. Patent and Trademark Office upon request and payment of the necessary fee.

FIG. 1 shows the classification of morphological blastocyst grades. ICM/Inner Cell Mass: the more and the more tightly packed the cells, the higher the grade thereof. Trophectoderm: the more and the more tightly packed the cells, the higher the grade thereof.

FIG. 8 shows norepinephrine values in culture solutions and blood hormone values, divided based on whether the blastocyst growth was good or not and on the presence of implantation after blastocyst transfer. A marked difference was observed in the value of norepinephrine secreted into the culture solutions between cases grown to pregnancy/delivery and cases showing no implantation.

FIG. 9 is a series of photographs showing the expression of dopamine β-hydroxylase as a norepinephrine synthetase in mouse blastocysts using an immunofluorescent staining method. A: expanded blastocysts. B: hatching blastocysts.

FIG. 13 is a table showing the in vitro development rates of in vitro fertilized mouse embryos cultured in vitro under conditions of various concentrations of norepinephrine.

MODE OF CARRYING OUT THE INVENTION

Figure 2:
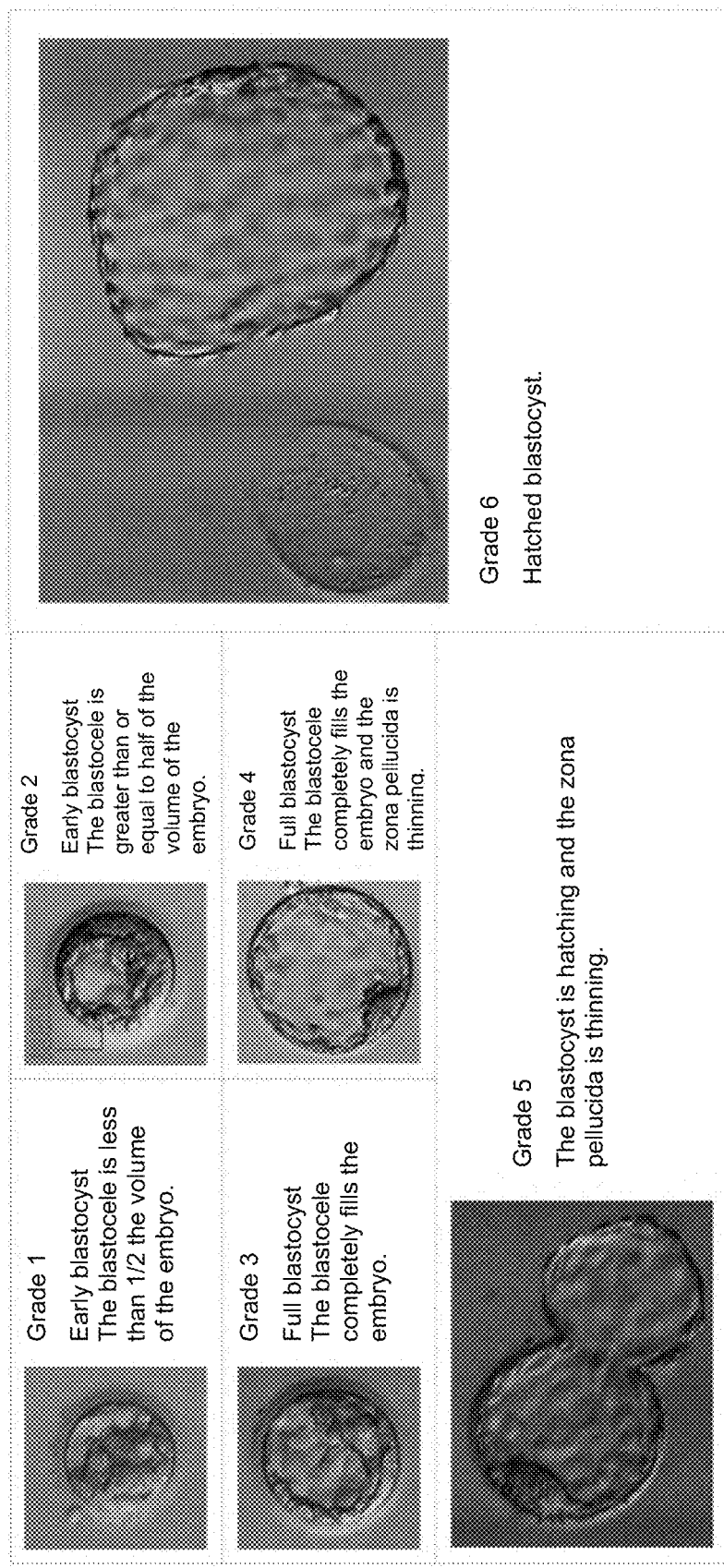
FIG. 2 shows Gardner's evaluation of blastocysts. Stages of blastocyst growth are represented by grades.
Figure 3:
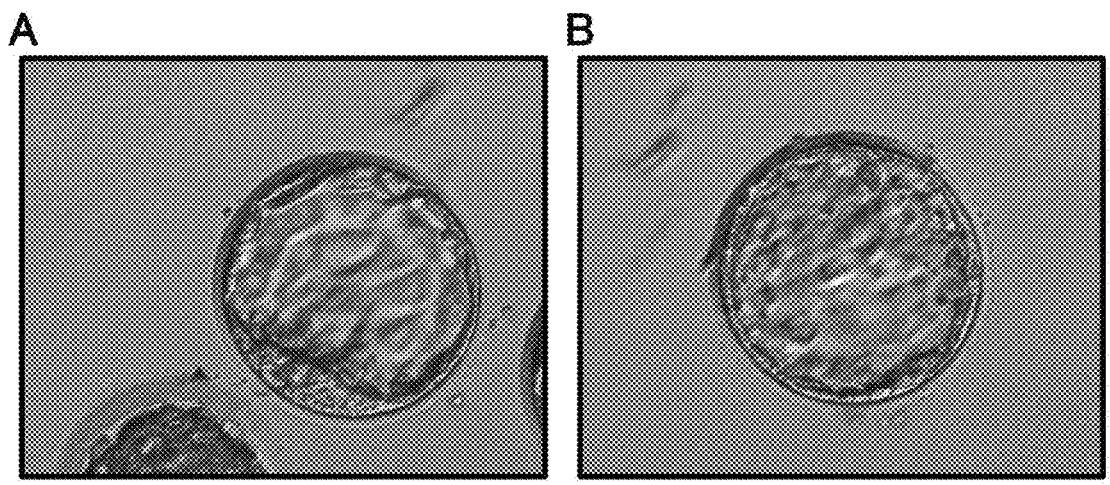
FIG. 3 shows blastocysts derived from the same patient receiving transfer. Frozen embryos were used for both first and second transfers. A: used for the second transfer, resulting in implantation-pregnancy. B: used for the first transfer, not resulting in pregnancy. A and B were both derived from ova collected at the same cycle in the same patient and frozen at the same growth rate and at the same point in time (at 123 hours after in vitro fertilization) in an in vitro culture solution, and had the same diameter (160 μm).
Figure 4:
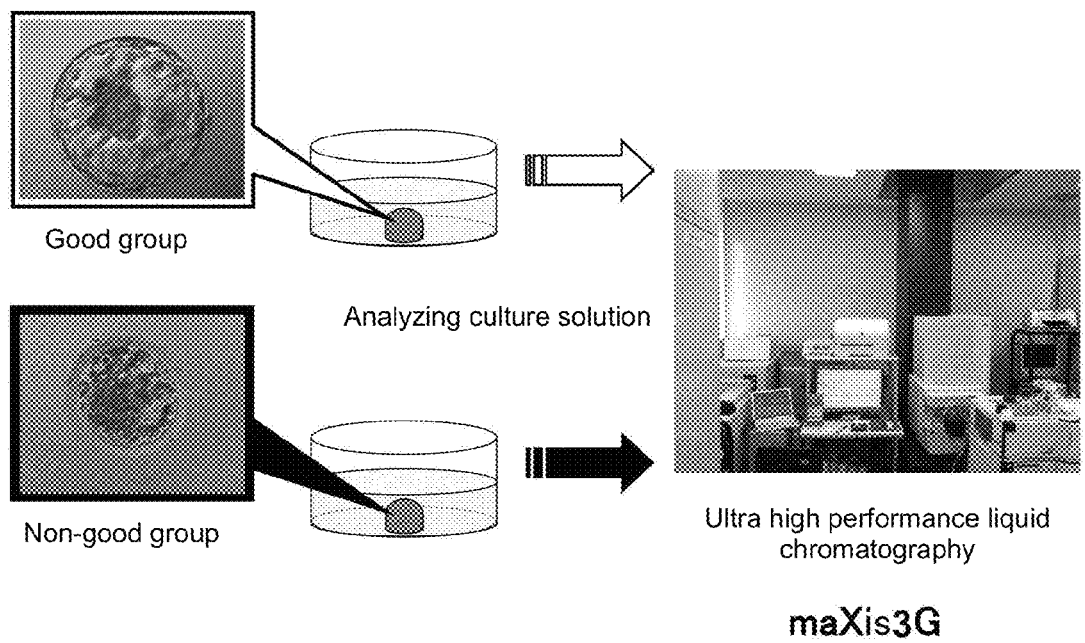
FIG. 4 shows the schematic of a method for evaluating blastocysts. Ultra high performance liquid chromatography, maXis™ 3G (from Bruker Daltonics), was used.
Figure 5:
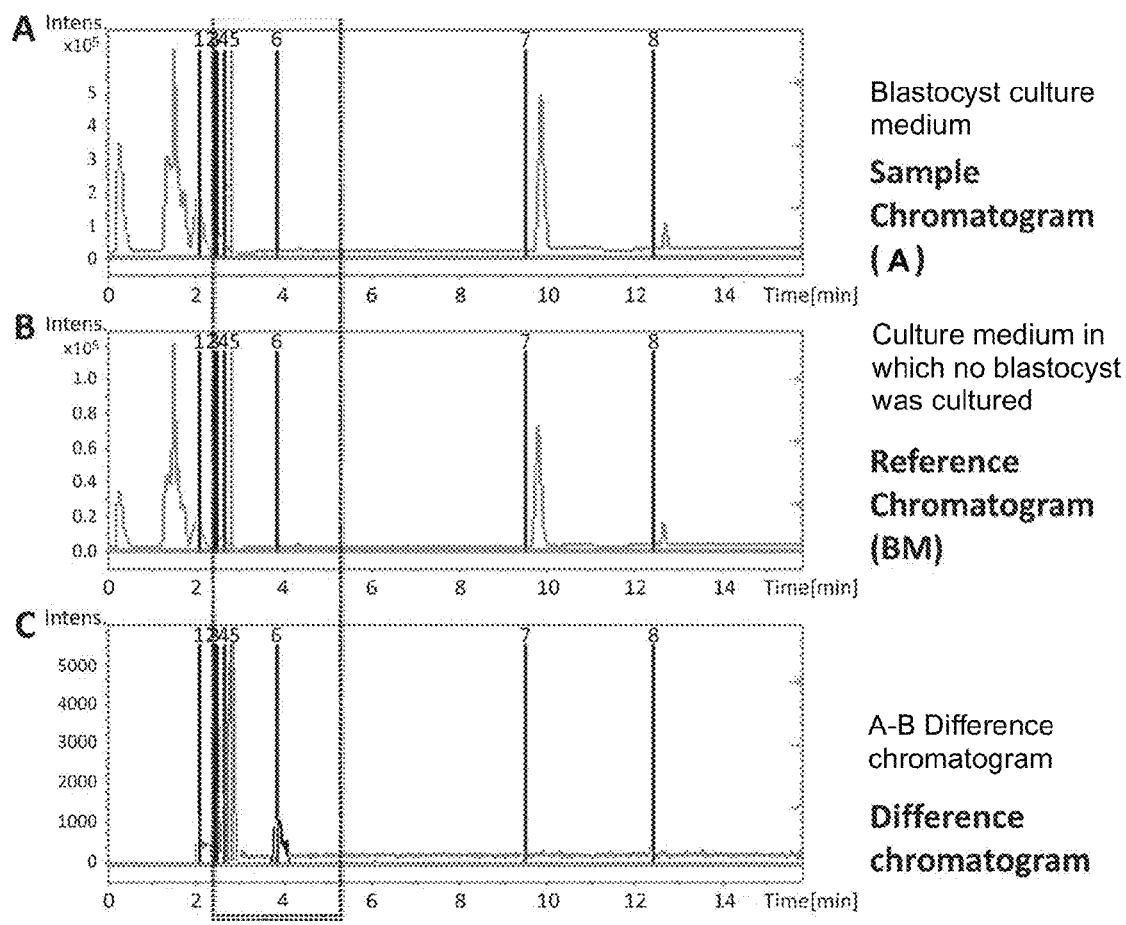
FIG. 5 shows chromatograms of a culture solution in which blastocysts were cultured and a culture solution in which no culture was performed (control). A: blastocyst culture medium. B: culture medium in which no blastocyst was cultured. C: peak difference between A and B. Marked peak differences were confirmed in peak 5 and peak 6.
Figure 6:
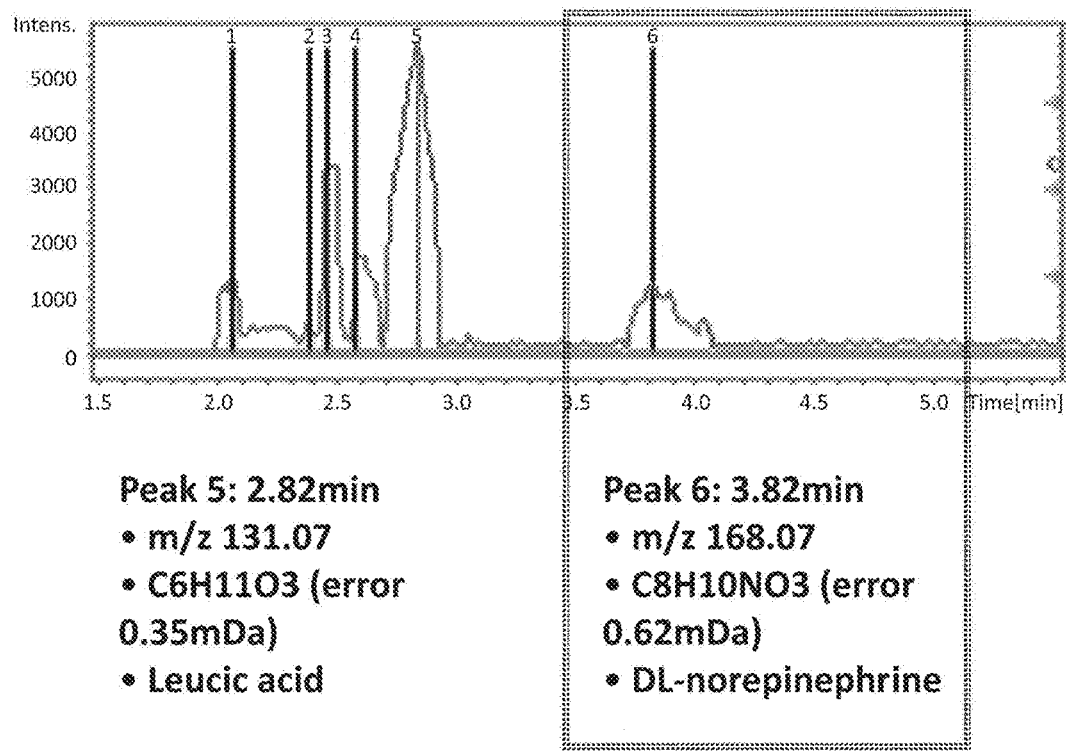
FIG. 6 shows identified secretory components of blastocysts. Peak 5 corresponded to leucic acid, and peak 6 corresponded to norepinephrine.
Figure 7:
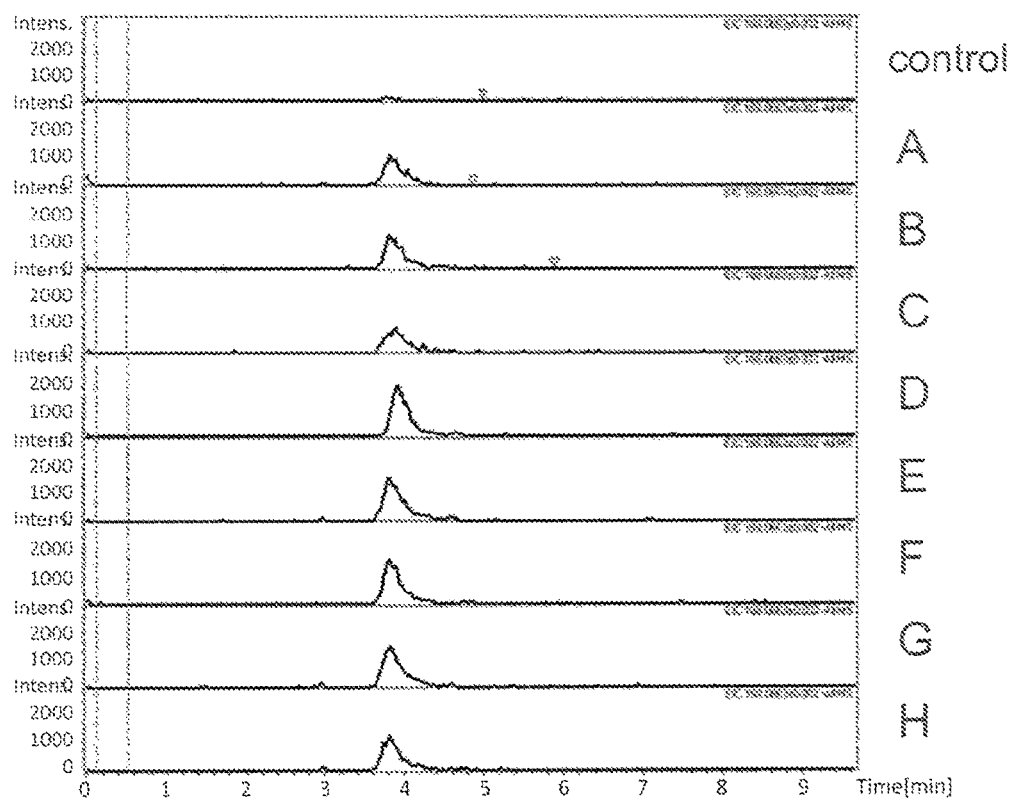
FIG. 7 shows peak waveforms in chromatograms of norepinephrine secreted into culture solutions, quantified as peak areas. Control: a culture solution in which no blastocyst was cultured.

The present invention is based on the identification of a biomarker in the fields of the medicine and biology of reproduction. Specifically, the quantitative determination of the value of norepinephrine provides information capable of predicting the results of in vitro fertilization-embryo transfer, and particularly predicting the quality of growth of a fertilized ovum and the success or failure of implantation of an embryo. In addition, this marker is useful for digitalizing the viability of an embryo and selecting an embryo with a high probability of implanting.

The method for evaluating transfer embryos according to the present invention (hereinafter also referred to as "the present evaluation method") is not particularly limited provided that it is a method involving quantitatively analyzing the norepinephrine value of test objects likely to contain norepinephrine released from the transfer embryos and predicting the quality of the transfer embryos from the analysis results obtained; the above-described norepinephrine is also known as noradrenaline.

In the present evaluation method, the method for quantitatively analyzing the norepinephrine value is not particularly limited provided that it is a method capable of quantitatively determining norepinephrine with high sensitivity and high selectivity; however, examples thereof can include high performance liquid chromatography/mass spectrometry, a chromatography method, an ELISA method, an electrochemiluminescent immunoassay (ECLIA), and a quantitative polymerase-chain-reaction method (qPCR). Among others, ultra high performance liquid chromatography/mass spectrometry can be preferably exemplified.

Examples of the transfer embryo can include a cleavage stage embryo as a fertilized ovum (embryo) at 2 to 3 days after starting cleavage, and a blastocyst cultured in vitro for 5 to 6 days; however, the blastocyst is preferable in terms of a high pregnancy rate. Humans can be preferably exemplified as the origin of the transfer embryo; however, other examples thereof can include mammals commonly used as experimental animals, domestic animals, and pets, such as rats, mice, rabbits, sheep, pigs, cows, horses, goats, cats, dogs, and monkeys.

Examples of the test object can include a culture solution of transfer embryos obtained by culturing fertilized ova (embryos) in a medium, or a processed product thereof. The medium may be a medium used in conventional tissue culture; examples thereof can include Quinn's Advantage Protein Plus Cleavage Medium (SAGE, IVF Inc., Trumbull, Conn., USA) as well as HTF (Human Tubal Fluid Medium), P1 medium, G1/G2 medium.

In a method of in vitro fertilization, for standard human in vitro fertilization (IVF), for example, 100,000 sperms are preferably co-cultured for each ovum at the MII stage cultured in 50 μL of Quinn's Advantage Protein Plus Cleavage Medium. Preferred examples of other methods of in vitro fertilization can include microinsemination (ICSI).

Examples of IVF providing fertilized ova during 18 to hours after co-culture with sperms or a method for culturing human fertilized ova obtained by microinsemination can include a method which involves performing culture in 20 μL of Quinn's Advantage Protein Plus Cleavage Medium for 2 days after fertilization, and while performing culture in 20 μL of Quinn's Advantage Blastocyst Medium (BM) from 2 days after fertilization until the 4-cell stage, exchanging a half volume (10 μL) of the BM culture solution with a fresh culture solution with the timing of 76 to 80 hours after fertilization, followed by culture in the identical culture solution until 80 to 170 hours after fertilization.

Examples of in vitro embryo culture environment can include conditions of 37.5° C., 5% $CO_2$, and 5% $O_2$.

Because frozen and thawed embryo transfer is clinically known to result in a high implantation rate compared to fresh embryo transfer, the grown fertilized ovum (embryo) is preferably once cryopreserved before transfer; preferred methods therefor can include a vitrification preservation method.

Preferred examples of the culture solution as a test object can include the above culture solution discarded in cryopreserving an embryo (20 μL for the above culture method), and preferred examples of a control analyte can include the BM culture solution in which no embryo is cultured.

In a preferable aspect, the step of quantitatively analyzing norepinephrine in a test object preferably uses an analysis method using the principle of chromatography combining high selectivity and high sensitivity in view of a predicted concentration of norepinephrine in the test object, and more preferably uses a method for separation/detection using ultra high performance liquid chromatography. Examples of a detector for ultra high performance liquid chromatography can include devices using optical properties (absorbance, refractive index, and fluorescence), electrochemical properties, mass spectrometry, and the like.

Because the test object is expected to have extremely many contaminating substances and large amounts of metabolites, comprehensive metabolic product analysis (metabolomics analysis) is preferably used for a method for analyzing the test object, and multivariate analysis is more preferably used for the analysis of data in simultaneously dealing with a flood of variables. Chromatogram data obtained by various above analysis methods need to be converted to numerical data for performing multivariate analysis; as an example of a method therefor can be mentioned first identifying peaks in data observed by chromatography and then calculating integrated peak areas to prepare a peak list.

The analysis of norepinephrine in a culture solution of blastocysts using the ultra high performance liquid chromatography maXis™ 3G produces the following findings.

(1) A norepinephrine level (peak area) below about 5,100 CPU in a culture solution of human blastocysts indicates good growth.

(2) A norepinephrine level (peak area) below about 2,400 CPU in a culture solution of human blastocysts indicates a high possibility of implantation and pregnancy when the embryo is transferred.

(3) A norepinephrine level (peak area) exceeding about 8,500 CPU in a culture solution of human blastocysts indicates poor growth or growth arrest, and a low possibility of implantation and pregnancy when the embryo is transferred.

The evaluation method may comprise a preceding step before obtaining a test object, and the test object may be directly used for analysis, or may be subjected to pretreatments, such as freezing, purification, and concentration.

Blastocyst transfer is preferably targeted at women desiring pregnancy.

The present invention will be more specifically described below with reference to Examples. However, these Examples are not intended to limit the technical scope of the present invention.

EXAMPLES

Example 1

In the following Examples, blastocysts and blastocyst culture solutions were used for the purpose of study approved by Institutional Review Board (IRB) with consent from patients receiving in vitro fertilization in Yamashita Shonan Yume Clinic, as donors.

1. Ovum Collection

Ovarian stimulation was carried out using a combination of clomiphene citrate (CC) (trade name: Clomid, Shionogi & Co., Ltd., Japan) and human menopausal gonadotropin (HMG) (trade name: Humegon, Organon International, Netherlands) or recombinant follicle-stimulating hormone (r-FSH) (trade name: Follistim, MSD K.K., Japan). CC was administered at a dose of 50 mg/day from 3 days after the start of menstruation until the day before oocyte maturation induction, and HMG or r-FSH was administered at a dose of 75 IU at intervals of 2 days from 8 days after the start of menstruation. The administration of HMG/r-FSH was adjusted depending on the follicle-stimulating hormone value and the estradiol (follicular hormone) value in the patient's serum and the results of diagnostic echo imaging. At the final stage of oocyte maturation, 600 μg of a gonadotropic hormone-releasing hormone (GnRE analog) (trade name: Sprecur, Aventis Pharma, Japan) was administered to sharply increase endogenous gonadotropin, and ova were sucked/recovered by puncturing an ovarian follicle in the ovary through the vagina while confirming it by a transvaginal ultrasonic image 34 to 35 hours after the administration of the GnRH analog and used for culture.

2. In Vitro Fertilization

The collected ova were subjected to standard in vitro fertilization (IVF) or microinsemination after recovery, based on clinical estimation. For the standard in vitro fertilization, the ova were cultured in 50 μL of Quinn's Advantage Protein Plus Cleavage Medium, and 100,000 sperms separately collected were co-cultured for each ovum at the MII stage. In the standard IVF, the ova become fertilized ova during 18 to 22 hours after the co-culture with the sperms, and human fertilized ova obtained by IVF or microinsemination were cultured in 20 μL of Quinn's Advantage Protein Plus Cleavage Medium for 2 days after fertilization. They were cultured in 20 μL of Quinn's Advantage Blastocyst Medium (BM) from 2 days after fertilization until the 4-cell stage, and a half volume (10 μL) of the BM culture solution was exchanged with a fresh culture solution with the timing of 76 to 80 hours after fertilization, followed by culture in an identical culture solution during 80 to 170 hours after fertilization. All culture steps were performed in an environment of 37.5° C., 5% $CO_2$, and 5% $O_2$.

3. Cryopreservation

Before cryopreserving the cultured embryos, the embryos were evaluated based on morphology and growth time. Well-grown embryos had morphologic grades 2 and 3, an average time of growth into blastocysts of 112 hours, and an average cryopreservation time of 121 hours. All embryos were cryopreserved by a vitrification preservation method until use for transfer. The culture solution usually discarded at the stage of cryopreservation was placed in a 1.0-mL Eppendorf tube and stored at −30° C. until it was used for the analysis of the present evaluation method.

4. Ultra High Performance Liquid Chromatography Analysis 4-1 Practice

The test objects of the culture solutions recovered and stored according to the above were analyzed using the ultra high performance liquid chromatography maXis™ 3G. A culture solution for which blastocysts were grown 5 days after fertilization and cryopreserved was called a good embryo culture solution section (section G), and a culture solution for which no blastocysts were grown even 7 days after fertilization was called a non-good embryo culture solution section (section NG). A BM culture solution in which embryo culture was not performed was called a control section (section C). Components specifically contained in 20 μL each of the sections G, NG, and C were identified and quantitatively determined by an LC-hybrid-MS method using the ultra high performance liquid chromatography maXis™ 3G (FIGS. 4 to 7).

4-2 Results

Norepinephrine was identified from the sections G (n=4) and NG (n=4), and not identified from the section C. As a result of quantitatively determining norepinephrine in the sections G and NG, the average result of the peak areas measured in positive mode was 3.97 E+4 CPU for the section G and 4.42 E+4 CPU for the section NG, and the average result of the peak areas measured in negative mode was 1.49 E+4 CPU for the section G and 2.20 E+4 CPU for the section NG. The released amount of norepinephrine tended to be more for the section NG in either mode. To examine effects of the expression level of norepinephrine on pregnancy, the norepinephrine level was compared between a section in which pregnancy continued after blastocyst transfer and a non-pregnancy section, among well-grown embryos; as a result, norepinephrine was detected for 23 (62%) of 37 human well-grown embryos and for 7 (100%) of 7 growth-stopped embryos. The norepinephrine level (peak area) was 5,101 CPU on average for the human well-grown embryos, while it was 8,502 CPU on average for growth-stopped embryos. The norepinephrine level was 1,458.8 CPU on average for the section in which pregnancy continued (11 cases), while it was 8,612.8 CPU on average for the non-pregnancy section (8 cases) (FIG. 8).

5. Immunofluorescent Staining 5-1 Practice

To examine whether norepinephrine was expressed in blastocysts, the immunofluorescent staining of dopamine β-hydroxylase (DBH) as a norepinephrine synthetase was performed in human well-grown embryos and growth-stopped embryos, mouse well-grown embryos and degenerated embryos, and rat well-grown embryos. The growth-stopped embryos and blastocysts were each washed 3 times with PBS containing 0.1% PVA; 2% (w/v) paraformaldehyde (Sigma) and 0.2% (v/v) TritonX-100 (Sigma) were each added to PBS-PVA; and the blastocysts were fixed at ordinary temperature for 60 minutes, followed by blocking with PBS containing 10% normal goat serum (NGS) at 4° C. for 40 minutes. A 1st antibody (DBH) was added to PBS-BSA to PBS-BSA:1st antibody=100:1, which was then incubated at 4° C. overnight (for 16 hours or more). A 2nd antibody (Alexa 488 anti-rabbit IgG) was added to PBS-BSA to PBS-BSA: 2nd antibody=100:1, which was then allowed to stand at ordinary temperature for 60 minutes. Nuclei were stained with 1 μM PI (propidium iodide). Then, the embryos were each whole-mounted on a slide glass using Vectashield® (Vector Laboratories, Burlingame, Calif.). The slide was observed for the expression and localization of DBH under a confocal laser microscope (Laica Co, Ltd., DMI6000B, TCS-SP5). Each of the blastocysts and stopped embryos immunofluorescently stained with DBH (Alexa 488) and PI were analyzed at wavelengths of 500 to 535 nm and wavelengths of 555 to 700 nm, using the confocal laser microscope. Images were collected at intervals of 2 to 5 μm parallel to the equatorial plane.

5-2 Results

Figure 10:
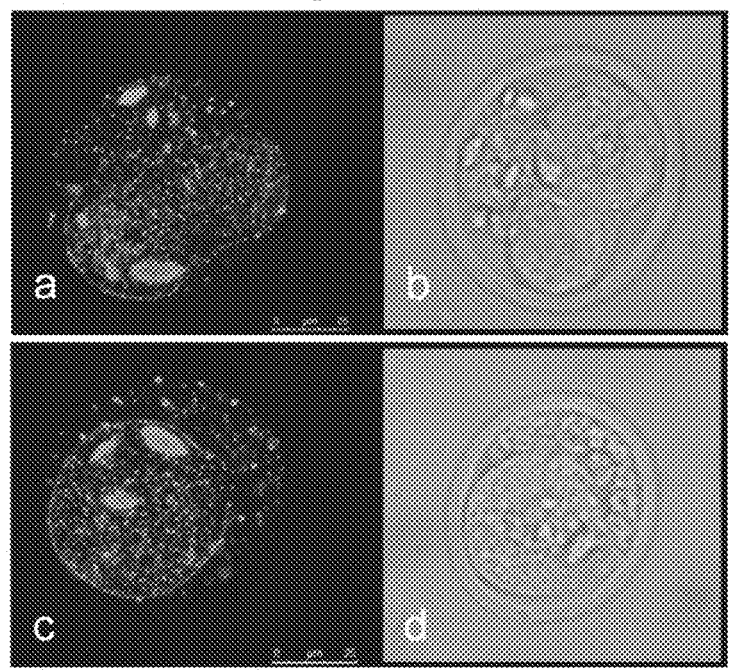
FIG. 10 is a series of photographs showing the expression of dopamine β-hydroxylase in mouse degenerated embryos using an immunofluorescent staining method. Dopamine β-hydroxylase is strongly expressed in blastomeres whose division is stopped.
Figure 11:
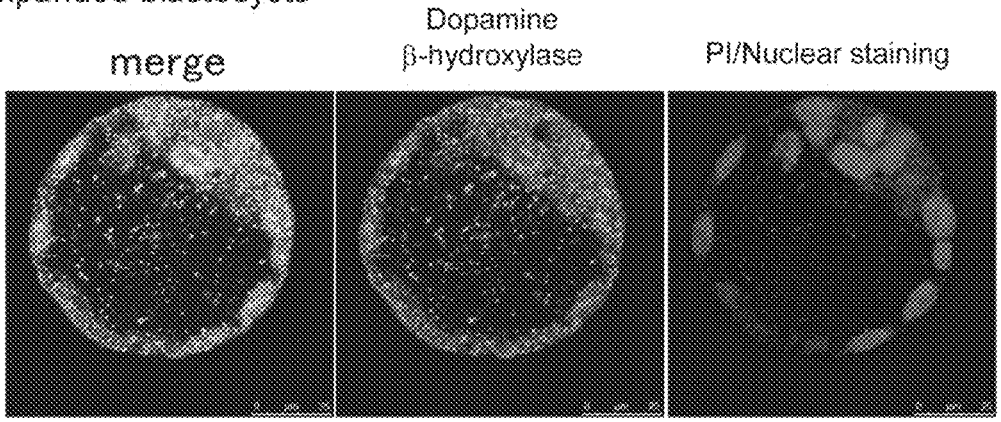
FIG. 11 is a series of photographs showing the expression of dopamine β-hydroxylase in expanded blastocysts of a rat using an immunofluorescent staining method.
Figure 12:
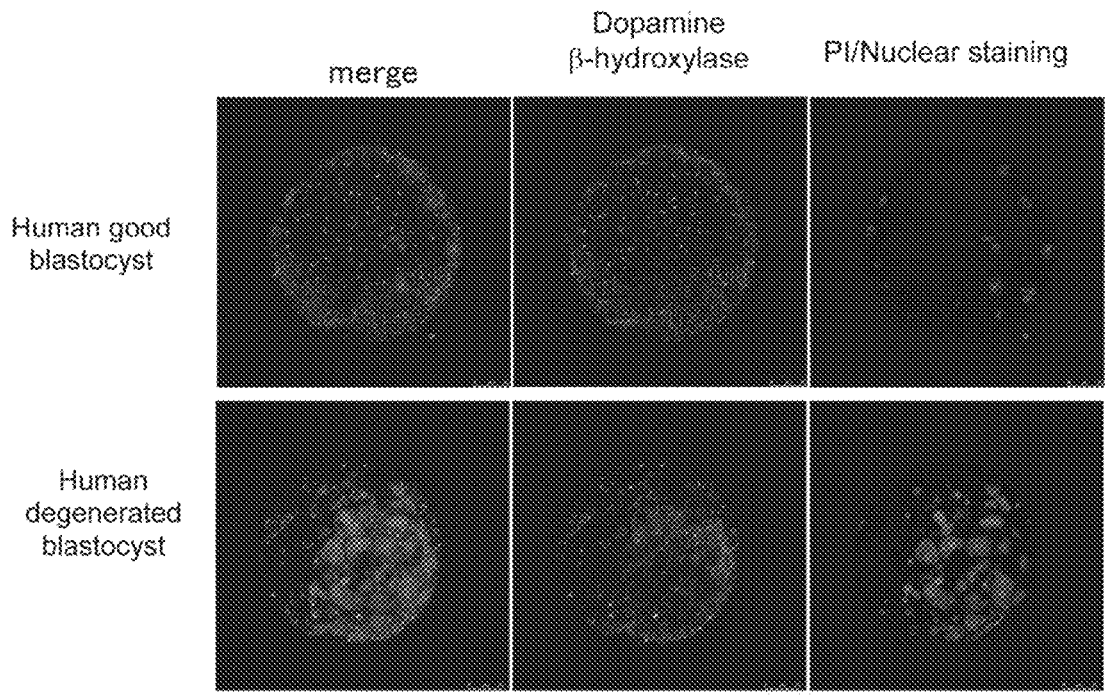
FIG. 12 is a series of photographs showing the expression of dopamine β-hydroxylase in a human well-grown blastocyst and a degenerated blastocyst using an immunofluorescent staining method.

In the images of immunofluorescently stained mouse blastocysts, DBH was dominantly expressed in inner cell mass at a low differentiation stage (FIG. 9A), while DBH could be confirmed to be expressed in the trophoblast as differentiation advanced (FIG. 9B). The well-grown embryo had a structure in which trophoblastic cells were in close contact with and connected to the inner cell mass, while from differential interference images and staining images, the mouse degenerated embryo was found to have a structure in which blastomeres whose division was stopped, strongly expressing DBH were separated in the central part (FIG. 10). In the images of stained rat blastocysts, as with the mouse, DBH was confirmed to be expressed on inner cell mass and trophoblast in a more differentiated good blastocyst (FIG. 11). In the images of stained human well-grown blastocysts and degenerated blastocysts, like the findings with the mouse and the rat, DBH could be confirmed to be expressed in both inner cell mass and trophoblastic cells in good blastocysts, while it was not only confirmed to be strongly expressed in blastomeres whose division was stopped but also confirmed to be extracellularly expressed in degenerated blastocysts (FIG. 12). Thus, for blastocysts of mammals including a human, it was shown that a well-grown blastocyst expressed DBH in the trophoblastic cells in a stage in which differentiation advanced while a degenerated embryo strongly expressed DBH in blastomeres whose division was stopped.

6. In Vitro Culture of In Vitro Fertilized Mouse Embryo under Conditions of Various Concentrations of Norepinephrine 6-1 Practice In performing this experiment, mouse oocytes were recovered, subjected to in vitro fertilization, and cultured in vitro. Using male and female ICR mice (Japan SLC, Inc., Shizuoka, Japan), all mice were housed under ad libitum feeding with water and a commercial experimental solid feed and a controlled light and dark environment (light environment: from 7 a.m. to 9 p.m.) in a specific pathogen-free environment. All animal experiments in this Example were approved by Animal Research Committee, Azabu University and carried out based on the guidelines of the committee. The in vitro fertilization was performed by the above-described method. In preparation for oocyte collection, 7.5 IU of horse chorionic gonadotropin (eCG; PEAMEX, Nippon Zenyaku Kogyo Co., Ltd., Fukushima, Japan) was administered to female ICR mice, and 7.5 IU human chorionic gonadotropin (hCG; Novartis Pharma K.K., Tokyo, Japan) was then administered thereto 48 to 50 hours later to induce superovulation. Cumulus-oocyte complexes were transferred to a TYH culture solution and cultured. Sperms recovered from the cauda epididymis of mature male ICR mice were dispersed in a TYH culture solution and preincubated in an incubator set at 37° C. and 5% $CO_2$. Sperms before fertilization were adjusted to a final concentration of $3 \times 10^6$ sperms/mL in the TYH culture solution. After in vitro fertilization, oocytes in each of which the pronucleus divided into two nuclei could be confirmed were used for subsequent in vitro culture. The concentration of norepinephrine in KSOM culture solution was divided into 0 mM (control), 0.01 mM, 0.05 mM, 0.1 mM, and 1 mM, and fertilized ova were cultured under each condition for 5 days. All fertilized ova were cultured in an incubator at 37.5° C. and 5% $CO_2$.

6-2 Results

Figure 14:
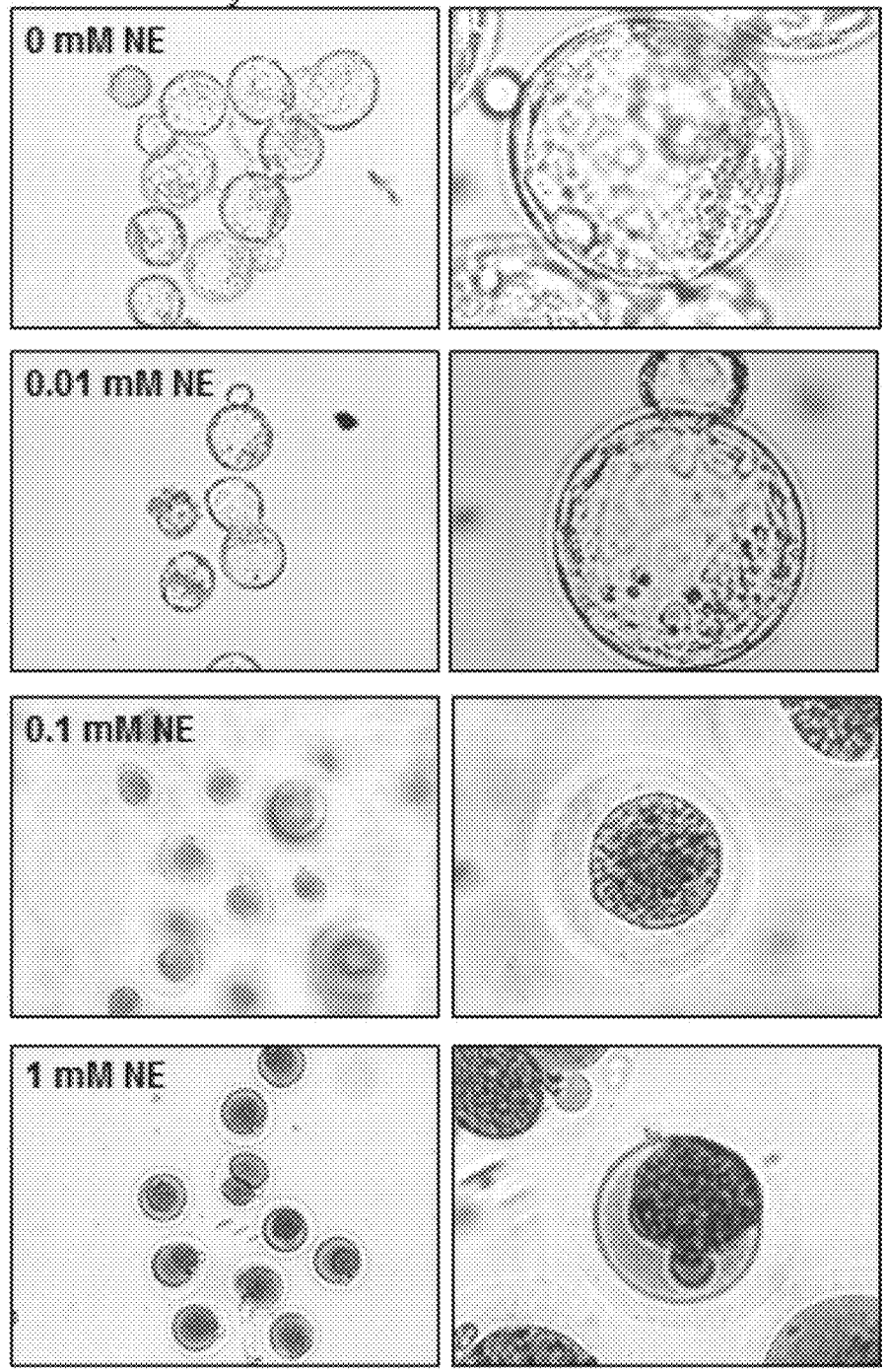
FIG. 14 is a series of photographs showing microscope images of in vitro fertilized mouse embryos cultured in vitro under conditions of various concentrations of norepinephrine.

Norepinephrine in the culture solution was shown to have a significantly negative effect on the development of fertilized ova (FIG. 13). It was shown that all embryos developed into the 4-cell stage were developed to blastocysts in the control culture solution containing no norepinephrine while only about 80%(41/51=the number of blastocysts/the number of 4-cell stage embryos) of embryos grown into the 4-cell stage were developed into blastocysts in the presence of 0.01 mM norepinephrine although the rate of being grown from pronucleus stage embryos into 4-cell stage embryos was slightly higher (89.5%) under conditions of the presence of even the low concentration of 0.01 mM norepinephrine than (86.9%) in control. A further higher concentration produced more significantly poor development; under conditions of 0.05 mM or more, the result was obtained that fertilized ova could not be developed into blastocysts. The photomicrographs of blastocysts cultured at each concentration of norepinephrine are shown in FIG. 14. Blastocysts could be confirmed in control and under culture conditions of a norepinephrine concentration of 0.01 mM; however, only degenerated blastocysts were observed under conditions of 0.1 mM and 1 mM. Thus, not only endogenous norepinephrine produced and secreted from fertilized ova but also, as shown by these results, exogenous norepinephrine were also demonstrated to have an influence on whether the development of fertilized ova was good or not. These results support that the quantitative determination of norepinephrine according to the present invention provides an important indication in predicting success or failure in the development of fertilized ova and the quality of a transfer embryo.

INDUSTRIAL APPLICABILITY

The present invention is expected to provide a new biomarker for non-invasively evaluating embryos with a precision impossible by existing morphological methods in in vitro fertilization-embryo transfer therapy as one of assisted reproduction technologies, and also expected to contribute to the development of a technique for sorting an embryo with a higher implantation rate and eventually cost burden relief on patients under fertility treatment.

The invention claimed is:

1. A method of transfer embryo evaluation for in vitro fertilization-embryo transfer therapy, the method comprising the steps of:
    (1) providing a test object containing norepinephrine released from a transfer embryo obtained from a subject;
    (2) measuring norepinephrine amounts in the test object;

(3) identifying that the transfer embryo is of high quality for growth in utero based on the measured norepinephrine amounts obtained in step (2); and (4) transferring the transfer embryo into a suitable female recipient for implantation, after identifying that the transfer embryo is of high quality for growth in utero and/or that the transfer embryo will support a viable pregnancy based on step (3).

2. The method according to claim 1, wherein the test object is a culture solution of the transfer embryo.

3. The method according to claim 2, wherein the transfer embryo is a human blastocyst.

4. The method according to claim 3, wherein the measuring step is a combination of ultra high performance liquid chromatography and mass spectrometry and comprises a step of quantifying the amount of norepinephrine by peak area values by multivariate analysis of the analysis results.

5. The method according to claim 3, wherein an amount of norepinephrine (peak area) below 5,100 counts per unit (CPU) indicates a high quality of growth in utero of the human blastocyst, and an amount of norepinephrine below 2,400 CPU indicates a high probability of a viable pregnancy after blastocyst transfer.

6. The method according to claim 2, wherein the measuring step is a combination of ultra high performance liquid chromatography and mass spectrometry and comprises a step of quantifying the amount of norepinephrine by peak area values by multivariate analysis of the analysis results.

7. The method according to claim 6, wherein the transfer embryo is a human blastocyst and an amount of norepinephrine (peak area) below 5,100 counts per unit (CPU) indicates a high quality of growth in utero of the human blastocyst, and an amount of norepinephrine below 2,400 CPU indicates a high probability of a viable pregnancy after blastocyst transfer.

8. The method according to claim 6, wherein the transfer embryo is a human blastocyst and an amount of norepinephrine (peak area) exceeding 8,500 counts per unit (CPU) indicates that growth of the human blastocyst has stopped, or that the human blastocyst has a low probability of supporting a viable pregnancy after blastocyst transfer.

9. The method according to claim 1, wherein the transfer embryo is a human blastocyst.

10. The method according to claim 9, wherein an amount of norepinephrine (peak area) below 5,100 counts per unit (CPU) indicates a high quality of growth in utero of the human blastocyst, and an amount of norepinephrine below 2,400 CPU indicates a high probability of a viable pregnancy after blastocyst transfer.

11. The method according to claim 3, wherein an amount of norepinephrine (peak area) exceeding 8,500 counts per unit (CPU) indicates that growth of the human blastocyst has stopped, or that the human blastocyst has a low probability of supporting a viable pregnancy after blastocyst transfer.

12. The method according to claim 9, wherein the measuring step is a combination of ultra high performance liquid chromatography and mass spectrometry and comprises a step of quantifying the amount of norepinephrine by peak area values by multivariate analysis of the analysis results.

13. The method according to claim 1, wherein the measuring step is a combination of ultra high performance liquid chromatography and mass spectrometry and comprises a step of quantifying the amount of norepinephrine by peak area values by multivariate analysis of the analysis results.

14. The method according to claim 13, wherein the transfer embryo is a human blastocyst and an amount of norepinephrine (peak area) below 5,100 counts per unit (CPU) indicates a high quality of growth in utero of the human blastocyst, and an amount of norepinephrine below 2,400 CPU indicates a high probability of a viable pregnancy after blastocyst transfer.

15. The method according to claim 13, wherein the transfer embryo is a human blastocyst and an amount of norepinephrine (peak area) exceeding 8,500 counts per unit (CPU) indicates that growth of the human blastocyst has stopped, or that the human blastocyst has a low probability of supporting a viable pregnancy after blastocyst transfer.

* * * * *